United States Patent [19]

Lee et al.

[11] Patent Number: 5,683,963
[45] Date of Patent: Nov. 4, 1997

[54] HERBICIDAL RIBOFURANOSE DERIVATIVES

[75] Inventors: Shy-Fuh Lee, Sunnyvale; Richard J. Anderson, Palo Alto, both of Calif.

[73] Assignee: Sandoz Ltd., Basel, Switzerland

[21] Appl. No.: 631,488

[22] Filed: Apr. 12, 1996

Related U.S. Application Data

[63] Continuation-in-part of Ser. No. 315,796, Sep. 20, 1994, abandoned.

[51] Int. Cl.$^6$ .......................... A01N 43/50; A01N 57/16; C07D 491/107; C07F 9/6561
[52] U.S. Cl. .......................... 504/196; 504/278; 548/119; 548/301.4
[58] Field of Search .................................. 504/196, 278; 548/119, 301.4

[56] References Cited

U.S. PATENT DOCUMENTS 5,354,868  10/1994  Harrington et al. ................. 548/301.4

FOREIGN PATENT DOCUMENTS

| 4129616 | 9/1990 | Germany . |
| 4129728 | 9/1990 | Germany . |
| 2085287 | 3/1990 | Japan . |
| 4154761 | 3/1990 | Japan . |
| 2167283 | 6/1990 | Japan . |

OTHER PUBLICATIONS

Fonne-Pfister et al, "The Mode of Action and, etc" CA 125: 188268 (1996).

Mizakai et al, "Preparation of 2-(hydroxymethyl)-1-oxa, etc" CA 114: 81826 (1991) RN 130509-63-6.

*Primary Examiner*—Patricia L. Morris
*Attorney, Agent, or Firm*—Lynn Marcus-Wyner

[57] ABSTRACT

The present invention relates to herbicidal ribofuranose derivatives, particularly hydantocidin derivatives, compositions comprising said derivatives and methods of use.

21 Claims, No Drawings

HERBICIDAL RIBOFURANOSE DERIVATIVES

This application is a continuation-in-part application of application Ser. No. 08/315,796, filed Sep. 20, 1994, now abandoned.

BACKGROUND OF THE INVENTION

This invention relates to herbicidal ribofuranose derivatives, and particularly to hydantocidin derivatives, compositions comprising said derivatives and methods of treating weeds utilizing the application of said derivatives to a locus where control is desired.

Various herbicidal spiro (hydantoin-tetrahydrofuran) derivatives are known, for example, hydantoin compounds disclosed in JP 2167283 (Jun. 27, 1990); JP 4154761 (May 27, 1992), and JP 2085287 (Mar. 26, 1990) (Sankyo), and also DE 4129728 and DE 4129616 (Ciba-Geigy).

DESCRIPTION OF THE INVENTION

It has now been discovered that certain novel ribofuranose derivatives have good herbicidal and plant growth regulating activity when applied either pre or post emergence, but particularly post emergence and when used against annual and perennial grasses and broad leaf weeds.

The terms "herbicide" and "herbicidal" are used herein to denote the inhibitive control or modification of undesired plant growth. Inhibitive control and modification includes all derivations from natural development such as for example, total killing, growth retardation, defoliation, desiccation, regulation, stunting, tillering, stimulation, leaf burn and dwarfing. The term "herbicidally effective amount" is used to denote any amount which achieves such control or modification when applied to undesired plants themselves or to the area in which these planks are growing. The term "plants" is intended to include germinant seed, emerging seedlings, and established vegetation, including roots and above ground portions.

The compounds of this invention are ribofuranose derivatives of formula I

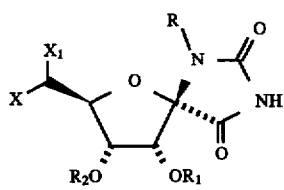

wherein

R, $R_1$ and $R_2$ are independently H and lower alkylcarbonyl;

$X_1$ is H or halogen;

X is halogen, —$SC(O)R_3$, $N_3$, —$OSO_2R_3$, —$OPO_3(R_7)_2$, $R_4R_5NO$, —$ONO_2$, —$P(O)R_6OH$, $CHX_2PO_3H_2$, and $CHX_2P(O)R_6OH$;

$R_3$ is lower alkyl and lower haloalkyl;

$R_4$ and $R_5$ are independently H and lower alkylcarbonyl or $R_4$ and $R_5$ taken together form phthaloyl;

$R_6$ is H, OH or lower alkyl;

$R_7$ is H, alkali or alkaline earth cation, ammonium cation or substituted ammonium cation; and $X_2$ is H or halogen.

The term "alkyl" refers to straight, branched and cyclo groups, preferably con mining up to 4 carbon atoms. This applies to all alkyl moieties contained for example in haloalkyl and alkylcarbonyl.

Suitable halogen groups include fluorine, chlorine, bromine and iodine. Haloalkyl groups may be substituted by one or more halogen atoms.

The term "substituted ammonia cation" refers to an ammonium cation substituted by a $C_1$–$C_6$alkyl, $diC_1$–$C_6$alkyl, $triC_1$–$C_6$alkyl, tetra $C_1$–$C_6$alkyl, hydroxy $C_1$–$C_5$alkyl, di(hydroxy $C_1$–$C_5$-alkyl), tri(hydroxy $C_1$–$C_5$alkyl), $C_1$–$C_4$alkoxy $C_1$–$C_4$alkyl, hydroxy $C_1$–$C_4$alkoxy $C_1$–$C_4$alkyl or $C_1$–$C_4$alkoxy carbonyl $C_1$–$C_4$alkyl group.

Preferred sub-groups of compounds of formula I include the following compounds:

R, $R_1$ and $R_2$ are independently H and acetyl.

$X_1$ is H or fluoro.

When $X_1$ is H, X is preferably halogen, $SC(O)R_3$, $OSO_2R_3$, $ONO_2$, $OPO_3H_2$, $OPO_3Na_2$, $R_4R_5NO$, and —$P(O)R_6OH$.

When $X_1$ is halogen, X is preferably —$CHX_2PO_3H_2$ and —$CHX_2P(O)R_6OH$.

$R_3$ is $CH_3$ or $CF_3$.

$R_7$ is H, Na, $NH_4$, K, Ca and Mg.

A preferred sub-group of compounds of formula I include R, $R_1$ and $R_2$ independently H and lower alkylcarbonyl, preferably acetyl; $X_1$ is H; X is halogen, —$SC(O)R_3$, —$OSO_2R_3$, —$OPO_3H_2$, —$OPO_3Na_2$, $R_4R_5NO$, $N_3$, —$P(O)R_6OH$, —$ONO_2$, —$CHX_2PO_3H_2$, and —$CHX_2P(O)R_6OH$; $R_3$ is lower alkyl and lower haloalkyl; $R_4$ and $R_5$ independently H and lower alkylcarbonyl; $R_6$ is H, OH or lower alkyl and $X_2$ is H or halogen.

Another preferred sub-group of compounds of formula I include R is acetyl; $R_1$ is acetyl or H; $R_2$ is acetyl or H; $X_1$ is hydrogen or fluoro; X is halogen, $SC(O)R_3$, $OPO_3H_2$, —$ONO_2$, $OSO_2R_3$, $N_3$, $P(O)R_6OH$ and $R_4R_5NO$; $R_3$ is $CH_3$ or $CF_3$; $R_4$ and $R_5$ taken together form and $R_6$ is H, OH or ($C_1$–$C_4$) alkyl.

General processes for making the compounds of the invention are as follows:

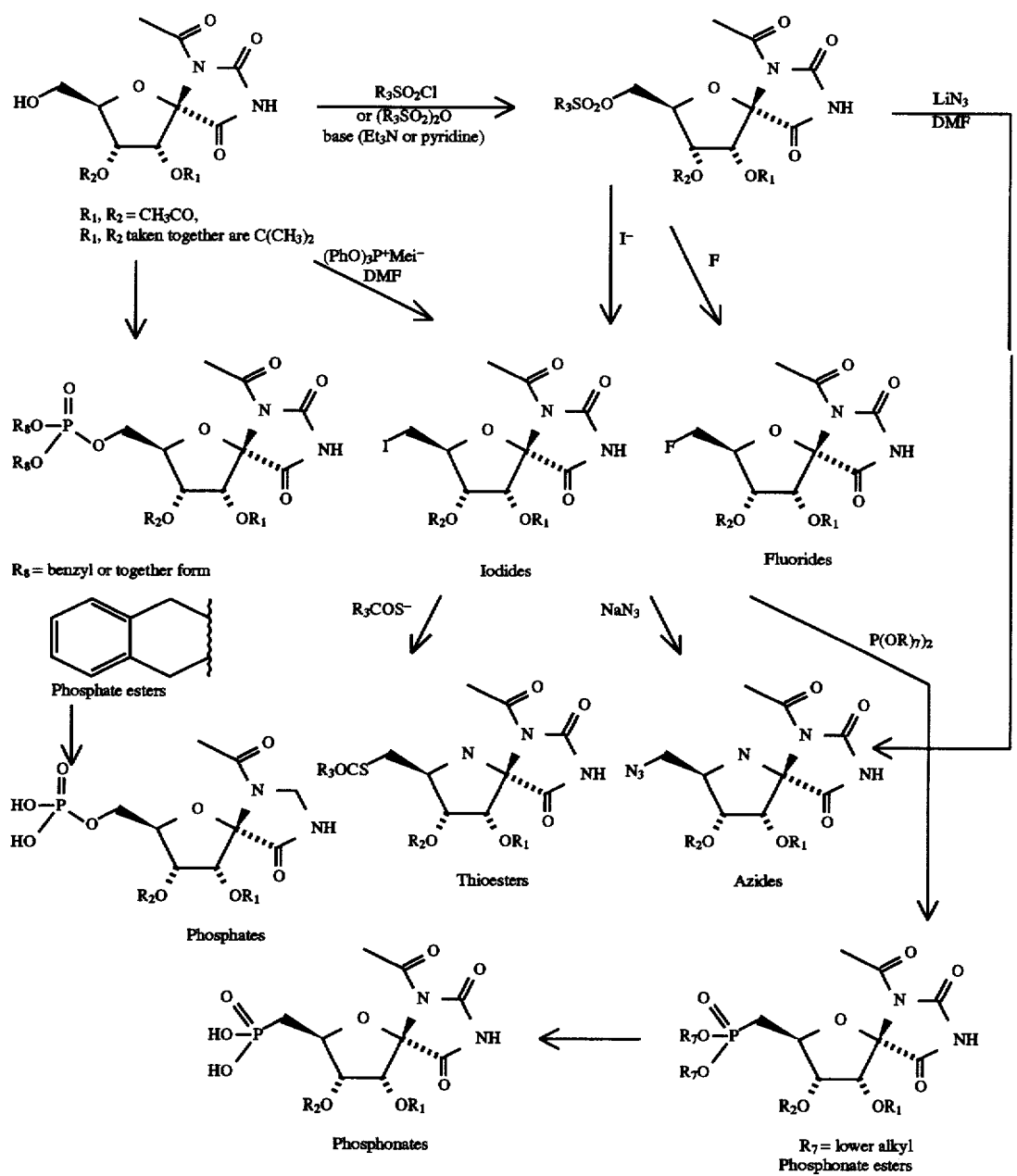
Synthesis of phthaloyl type compounds of the invention includes the general following scheme.
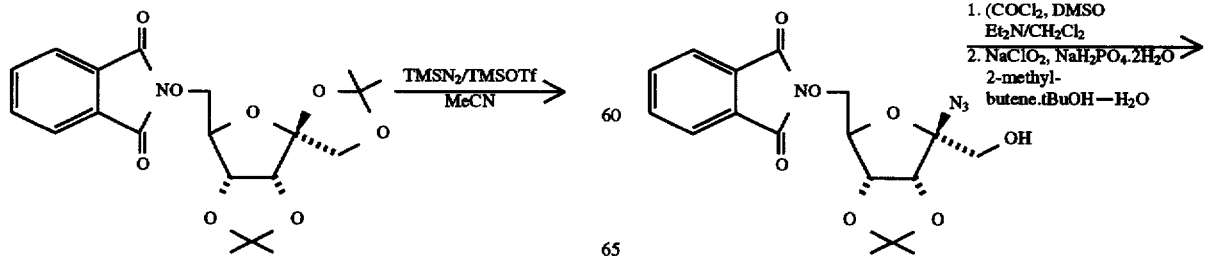

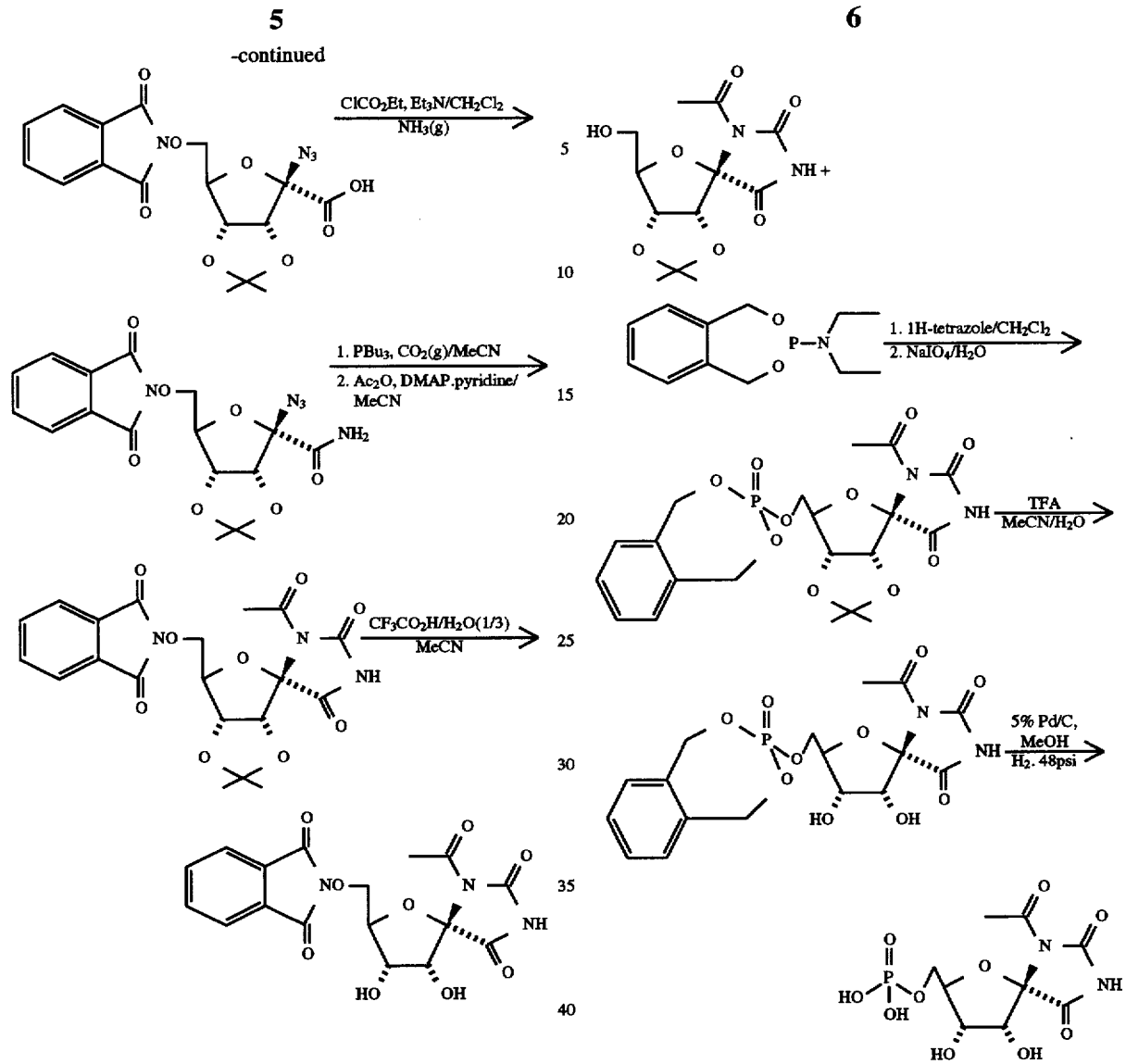

The following abbreviations are used herein:

DMF: means N,N-Dimethylformamide;

TMSN$_3$: means Trimethylsilyl azide;

TMSOTf: means Trimethylsilyl trifluoromethane-sulfonate;

DMAP: means 4-Dimethylaminopyridine; and

DMSO: means Dimethyl sulfoxide.

The process for making the compounds of this invention will be more fully understood by reference to the following examples.

EXAMPLE 1

Synthesis of 5'-Phosphono-N-acetyl-hydantocidin, Compound 2 in Table 1.

a. To a solution of (2R,3R,4R,5S)-6-acetyl-2-hydroxymethyl-3,4-isopropylidenedioxy-1-oxa-6,8-diazaspiro(4,4) nonane-7,9-dione (500 mg, 1.67 mm) and 1H-tetrazole (350 mg, 4.99 mm) in dichlormmethane (40 ml) is added, under nitrogen, at r.t. a solution of N,N-diethyl-1, 5-dihydro-2, 4, 3-benzodioxaphosphepin-3-amine (598 mg, 2.50) in dichloromethane (2 ml). The resulting mixture is stirred for 30 minutes and a solution of sodium periodate (1.2 g, 5.61 mm) in water (20 ml) is added. After stirring at r.t. for three hours, the reaction mixture is poured into water and extracted with dichloromethane. The combined extracts are washed with brine, dried and evaporated to dryness to give the crude product as white solid. The crude product is washed with dichloromethane to yield pure (2R,3R,4R,5S)-6-acetyl-2-(1,5-dihydro-2,4,3-benzodioxaphosphonoxymethyl)-3,4-isopropylidenedioxy-1-oxa-6,8-diazaspiro (4,4) nonane-7, 9-dione (554 mg).

b. The above phosphate (450 mg) in acetonitrile (6 ml) is treated with aqueous trifluoroacetic acid (3:1) (6 ml) at r.t. for 24 hours, and then concentrated to dryness in vacuum. The crude product is purified by thin-layer chromatography to furnish (2R, 3R, 4R, 5S)-6-acetyl-2-(1,5-dihydro-2,4,3-benzodioxaphosphonoxymethyl)-3,4-dihydroxy-1-oxa-6, 8-diazaspiro (4,4) nonane-7,9-dione (300 mg) as a foam.

c. A mixture of the above diol (450 mg) and 5%Pd (400 mg) in methanol (60 ml) is hydrogenated at 48 psi for 72 hours. After filtration of the mixture, the filtrate is concentrated under reduced pressure to give hygroscopic foam of 5'-phosphono-N-acetyl-hydantocidin.

EXAMPLE 2

Synthesis of (2R, 3R, 4R, 5S)-6-acetyl-2-phosphonoxymethyl-3, 4-diacetoxy-1-oxa-6,8-diazaspiro (4,4) nonane-7,9-dione, Compound 3 in Table 1.

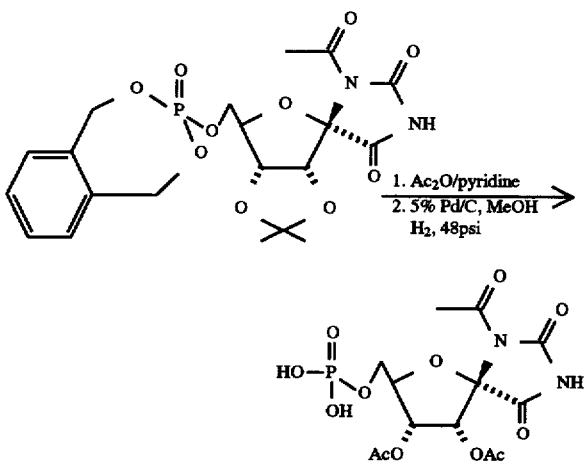

A solution of (2R,3R,4R,5S)-6-acetyl-2-(1,5-dihydro-2,4,3-benzodioxa-phosphonoxymethyl)-3,4-dihydroxy-1-oxa-6,8-diazaspiro (4,4) nonane-7,9-dione (400 mg) in pyridine (4 ml) is treated with acetic anhydride (0.5 ml) at r.t. for 48 hours, and then concentrated to dryness in vacuum at 45° C. The residue is taken up in dichloromethane, washed with dilute aqueous hydrochloric acid, brine, dried and evaporated to dryness. The crude product was purified by thin-layer chromatography to give (2R, 3R, 4R, 5S)-6-acetyl-2-(1,5-dihydro-2,4-3-benzoclioxaphosphonoxymethyl)-3,4-diacetoxy-1-oxa-6,8-diazaspiro(4,4)nonane-7,9-dione (320 mg) which is hydrogenated at 48 psi in methanol in the presence of 200 mg of 5% Pd/C for 48 hours. After filtration and evaporation, (2R, 3R, 4R, 5S)-6-acetyl-2-phosphonoxylmethyl-3,4-diacetoxy-1-oxa-6, 8-diazaspiro (4,4)nonane-7,9-dione (220 mg) is obtained as a hygroscopic foam.

EXAMPLE 3

Synthesis of (2R, 3R, 4R. 5S)-6-acetyl-2-acetylthiomethyl-3. 4-diacetoxy-1 -oxa-6,8-diazaspiro (4,4) nonane-7, 9-dione- Compound 5 in Table 1.

To a solution of (2R, 3R, 4R, 5S)-6-acetyl-2-iodomethyl-3, 4-diacetoxy-1-oxa-6,8-diazaspiro (4,4) nonane-7, 9-dione (598 mg, 1.32 mm) in anhydrous DME (10 ml) is added, under $N_2$, tetramethylammonium thioacetate (353 mg, 2.37 mm) in one portion. The resulting mixture is heated at 45° C. for 4 hours, then diluted with dichloromethane and washed with brine, dried, and evaporated for dryness. The crude product is purified by thin-layer chromatography to give (2R, 3R, 4R, 5S)-6-acetyl-2-acetylthiomethyl-3, 4-diacetoxy-1-oxa-6, 8-diazaspiro (4,4) nonane-7, 9-dione (500 mg) as a hygroscopic foam.

EXAMPLE 4

Synthesis of (2R, 3R, 4R, 5S)-6-acetyl-2-trifluoromethylsulfonyloxymethyl-3, 4-diacetoxy-1-oxa-6, 8-diazaspiro (4,4) nonane-7,9-dione- Compound 8 in Table 1.

To a solution of (2R, 3R, 4R, 5S)-6-acetyl-2-hydroxymethyl-3,4-diacetoxy-1-oxa-6,8-diazaspiro (4,4) nonane-7, 9 dione (300 mg, 0.87 mm) and pyridine (0.14 ml, 1.74 mm) in dichloromethane (4 ml) was added at −15° C. (salt-ice bath) trifluoromethylsulfonic anhydride (0.26 ml, 1.52 mm). The resulting mixture is stirred at the same temperature for 1 hour, then diluted with ethylacetate and washed with water, brine, dried and evaporated to dryness. The crude product is purified by thin-layer chromatography to give (2R, 3R, 4R, 5S)-6-acetyl-2-trifluoromethylsulfonyloxymethyl-3,4-diacetoxy-1-oxa-6,8-diazaspiro (4,4)nonane-7, 9-dione (370 mg) as a hygroscopic foam.

EXAMPLE 5

Synthesis of sodium salt of 5'-O-phosphonohydantocidin, Compound 11 in Table 1

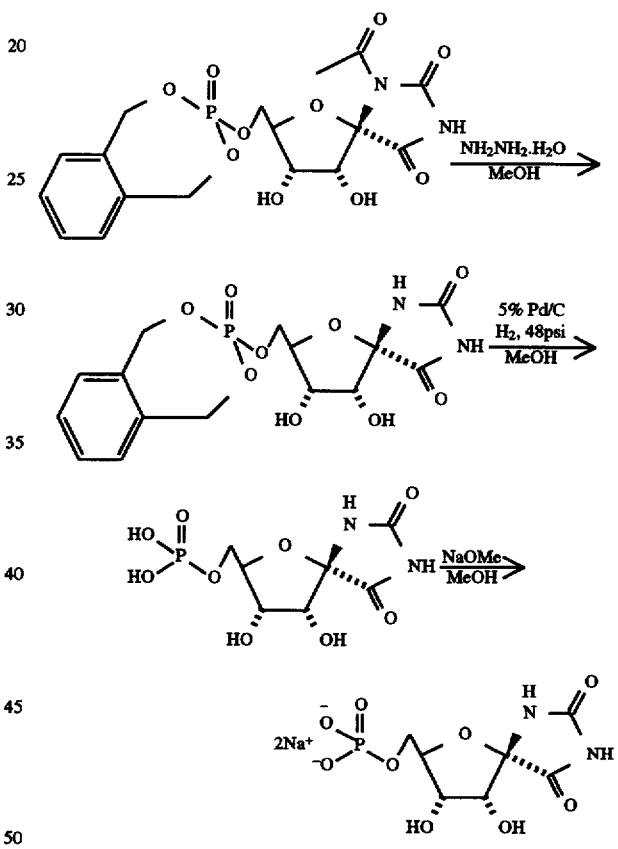

a) A solution of (2R,3R,4R,5S)-6-acetyl-2-(1,5-dihydro-2,4,3-benzodioxaphosphonoxymethyl)-3,4-dihydroxy-1-oxa-6,8-diazaspiro(4,4)nonane-7,9-dione (660 mg) and hydrazine monohydrate (134 mg) in methanol (30 ml) and dichloromethane (5 ml) was stirred at room temperature for 24 hours. The reaction mixture was then concentrated to dryness at room temperature to give oily residue which was purified by thin-layer chromatography to give (2R,3R,4R,5 S)-2-( 1,5-dihydro-2,4,3-benzodioxaphosphonoxymethyl)-3,4-dihydroxy-1-oxa-6,8-diazaspiro(4,4)nonane-7,9-dione (450 mg) as a foam, $[\alpha]_D=+13.46$ (MeOH).

b. A mixture of (2R,3R,4R,5S)-2-(1,5-dihydro-2,4,3-benzodioxaphosphonoxymethyl)-3,4-dihydroxy-1-oxa-6,8-diazaspiro (4,4)nonane-7,9-dione (450 mg) and 5% Pd/C (400 mg) in methanol (20 ml) and hydrazine monohydrate (134 mg) in methanol (30 ml) and dichloromethane (5 ml)

was stirred at room temperature to give oily residue which was purified by thin-layer chromatography to give (2R,3R,4R,5S)-2-(1,5-dihydro-2,4,3-benzodioxaphosphonoxymethyl)-3,4-dihydroxy-1-oxa-6,8-diazaspiro (4,4)nonane-7,9-dione (450 mg) as a foam, $[\alpha]_d=$ +13.46 (MeOH).

EXAMPLE 6

Synthesis of (2R,3R,4R,5S)-6-acetyl-2-nitrooxymethyl-3,4-dihydroxy-1-oxa-6,8-diazaspiro (4,4)nonane-7,9-dione, Compound 12 in Table 1

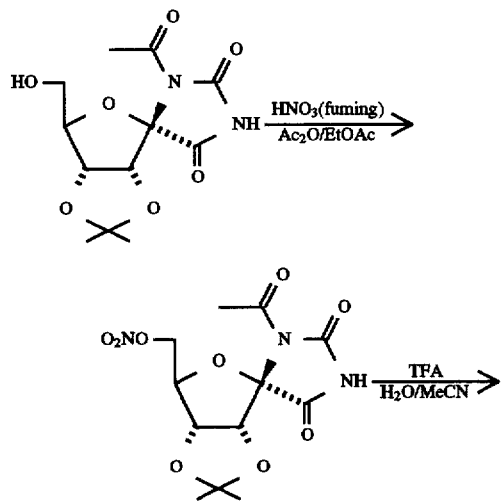

A cooled (-38° C.) (MeCN-CO$_2$) mixture of fuming nitric acid and acetic anhydride was added dropwise to a stirred solution of (2R,3R,4R,5S)-6-acetyl-2-hydroxymethyl-3,4-isopropylidenedioxy-1-oxa-6,8-diazaspiro (4,4)nonane-7,9-dione (675 mg) in anhydrous ethyl acetate (12 ml) at -30° C. The reaction mixture was stirred at -30° for 2 hours, then neutralized with solid sodium bicarbonate and stirred at room temperature for additional 20 minutes before dilution with ethyl acetate and filtration. The filtrate was washed with water, brine, dried and evaporated to dryness. The crude product was purified by preparative thin-layer chromatography to give 400 mg of (2R,3R,4R,5S)-6-acetyl-2-nitroxymethyl-3,4-isopropylidenedioxy-1-oxa-6,8-diazaspiro-(4,4) nonane-7,9-dione, m.p. 137° C., which was then dissolved in acetonitrile (6 ml) and treated with trifluoroacetic acid-water (1:3) (6 ml) at room temperature overnight. The reaction mixture was concentrated to dryness and purified by preparative thin-layer chromatography to give (2R,3R,4R,5S)-6-acetyl-2-nitrooxymethyl-3,4-dihydroxy- 1-oxa-6,8-diazaspiro(4,4)nonane-7,9-dione (240 mg) as a foam.

TABLE 1

| Cpd # | R | R$_1$ | R$_2$ | X$_1$ | H |
|---|---|---|---|---|---|
| 1 | CH$_3$CO— | H | H | H | (phthalimide-N-O) |
| 2 | CH$_3$CO— | H | H | H | —OPO$_3$H$_2$ |
| 3 | CH$_3$CO | CH$_3$CO | CH$_3$CO | H | —OPO$_3$H$_2$ |
| 4 | CH$_3$CO | CH$_3$CO | CH$_3$CO | H | I |
| 5 | CH$_3$CO | CH$_3$CO | CH$_3$CO | H | —SOCCH$_3$ |
| 6 | CH$_3$CO | H | H | H | —SOCCH$_3$ |
| 7 | CH$_3$CO | CH$_3$CO | CH$_3$CO | H | —(O)SO$_2$CH$_3$ |
| 8 | CH$_3$CO | CH$_3$CO | CH$_3$CO | H | —(O)SO$_2$CF$_3$ |
| 9 | H | CH$_3$CO | CH$_3$CO | H | —OH |
| 10 | H | H | H | H | —OPO$_3$H$_2$ |
| 11 | H | H | H | H | —OPO$_3$Na$_2$ |
| 12 | CH$_3$CO | H | H | H | —ONO$_2$ |
| 13 | CH$_3$CO | CH$_3$CO | CH$_3$CO | H | —ONO$_2$ |
| 14 | CH$_3$CO | CH$_3$CO | CH$_3$CO | H | —N$_3$ |
| 15 | CH$_3$CO | CH$_3$CO | CH$_3$CO | H | —F |

HERBICIDAL TESTS

EXAMPLE

Test compounds were weighed and dissolved in a stock solution consisting of acetone or DMSO:deionized water (1:1) and 0.5% adjuvant mixture. Dilutions from this stock solution were performed to allow for preparation of spray solutions consisting of single doses applied at a level equivalent to either 4.0, 1.0 or 0.25 kg/ha of active ingredient. The solutions were applied by a linear track sprayer set to deliver 1000 L/ha spray volume. Weed species tested are shown in Table 2. Herbicidal control was evaluated as % injury with 100% injury considered complete control.

In pre-emergent studies, each dose of herbicide was applied as a band treatment over the weed seed zone. Pots containing the seeds were then top-dressed with soil, the plants were grown in the greenhouse and visually evaluated 7 and 19 days after treatment. At an application rate of 1.0 kg/ha the Compounds 2, 3, and 8 exhibited herbicidal control at greater than 50% for all the grassy weeds tested.

In post-emergence studies, each dose of compound was applied to the foliage of the selected weed seedling species. The plants were allowed to grow in the greenhouse and visually evaluated at 1, 7 and 19 days after treatment. At an application rate of 1.0 kg/ha the compounds 2, 3, 5, 6, 7 and 8 exhibited herbicidal control at greater than 50% for all grassy weeds tested. Also control was exhibited in various broad leaf weeds.

TABLE 2

| Common Name | Genus Species |
| --- | --- |
| Velvetleaf | Abutilon theophrasti |
| Redroot Pigweed | Amaranthus retroflexus |
| Mustard White | Sinapis alba |
| Black Nightshade | Solanum nigrum |
| Wild Oat | Avena fatua |
| Downy Brome | Bromus tectorum |
| Barnyardgrass | Echinochloa crus-galli |
| Green Foxtail | Setaria viridis |

METHODS OF APPLICATION

Application of a compound of formula I is made according to conventional procedure to the weeds or their locus using a herbicidally effective amount of the compound, usually from 1 g to 10 kg/ha.

compounds according to the invention may be used for the control of both broadleaf and grassy weeds in both preplant incorporation and pre- and post-emergent application. Compounds may also exhibit selectivity in various crops and may thus be suited for use in weed control in crops such as but not limited to corn, cotton, wheat, soybean and rice.

The optimum usage of a compound of formula I is readily determined by one of ordinary skill in the art using routine testing such as greenhouse testing and small plot field testing. It will depend on the compound employed, the desired effect (a phytotoxic effect requiring a higher rate than a plant growth regulating effect), the conditions of treatment and the like. In general satisfactory phytotoxic effects are obtained when the compound of formula I is applied at a rate in the range of from 0.001 to 5.0 kg, more preferably of from 0.05 to 2.5 kg per hectare, especially 0.01 to 2.5 kg per hectare.

The compounds of formula I may be advantageously combined with other herbicides for broad spectrum weed control. Examples of herbicides which can be combined with a compound of the present invention include those selected from carbamates, thiocarbamates, chloroacetrimides, triazines, dinitroanilines, benzoic acids, glycerol ethers, pyridiazinones, uracils, phenoxys andureas for controlling a broad spectrum of weeds.

The compounds of formula I are conveniently employed as herbicidal compositions in association with agriculturally acceptable diluents. Such compositions also form part of the present invention. They may contain, aside from a compound of formula I as active agent, other active agents, such as herbicides or compounds having antidotal, fungicidal, insecticidal or insect attractant activity. They may be employed in either solid or liquid forms such as a wettable powder, an emulsifiable concentrate, a granule or a microcapsule incorporating conventional diluents. Such compositions may be produced in conventional manner, for example by mixing the active ingredient with a diluent and optionally other formulating ingredients such as surfactants.

Agriculturally acceptable additives may be employed in herbicidal compositions to improve the performance of the active ingredient and to reduce foaming, caking and corrosion, for example.

The term "diluent" as used herein means any liquid or solid agriculturally acceptable material which may be added to the active constituent to bring it in an easier or improved applicable form, respectively, to a usable or desirable strength of activity. It can for example be talc, kaolin, diatomaceous earth, xylene or water.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

Particularly formulations to be applied in spraying forms such as water dispersible concentrates or wettable powders may contain surfactants such as wetting and dispersing agents, for example the condensation product of formaldehyde with naphthylene sulphonate, an ethoxylated alkylphenol and an ethoxylated fatty alcohol.

In general, the formulations include from 0.01 to 99% by weight of active agent and from 0 to 20% by weight of agriculturally acceptable surfactant, and from 0.1 to 99.99% of solid or liquid diluent(s) the active agent consisting either of at least one compound of formula I or mixtures thereof with other active agents. Concentrate forms of compositions generally contain between about 2 and 95%, preferably between about 10 and 90% by weight of active agent.

Typical herbicidal compositions, according to this invention, are illustrated by the following Examples in which the quantities are in parts by weight.

EXAMPLE A

Preparation of a Soluble Powder

The water soluble compounds or their salts of this invention can be hammer milled to a screen size of 100 mesh. The resulting powder will readily dissolve in water for spraying.

EXAMPLE B

Preparation of a Wettable Powder

25 Parts of a compound of this invention are mixed and milled with 25 parts of synthetic free silica, 2 parts of sodium lauryl sulphate, 3 parts of sodium lignosulfonate and 45 parts of freely divided kaolin until the mean particle size is about 5 micron. The resulting wettable powder is diluted with water to a desired concentration.

What is claimed is:

1. A compound of the formula

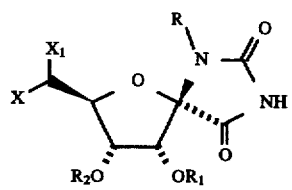

wherein

R, $R_1$ and $R_2$ are independently H and lower alkylcarbonyl;

$X_1$ is halogen;

X is halogen, —SC(O)$R_3$, —OSO$_2R_3$, —OPO$_3(R_7)_2$, $N_3$, $R_4R_5$NO, —ONO$_2$, —P(O)$R_6$OH, —CHX$_2$PO$_3H_2$, CHX$_2$P(O)$R_6$OH;

$R_3$ is lower alkyl or lower haloalkyl;

$R_4$ and $R_5$ are independently H and lower alkylcarbonyl or $R_4$ and $R_5$ taken together form phthaloyl;

$R_6$ is H, OH or lower alkyl;

$R_7$ is H alkali or alkaline earth cation, ammonium cation or substituted ammonium cation; and $X_2$ is H or halogen.

2. A compound according to claim 1 wherein $X_1$ is fluoro.

3. A compound according to claim 1 wherein R is acetyl or H.

4. A compound according to claim 1 wherein $R_1$ and $R_2$ are independently acetyl or H.

5. A compound according to claim 3 wherein $R_1$ and $R_2$ are acetyl.

6. A compound according to claim 1 wherein X is —$OSO_2R_3$.

7. A compound according to claim 1 wherein $R_3$ is $CH_3$ or $CF_3$.

8. A compound according to claim 1 wherein X is —$OPO_3H_2$ or —$OPO_3Na_2$.

9. A compound according to claim 1 wherein X is —$ONO_2$.

10. A compound according to claim 1 wherein R, $R_1$, and $R_2$ are independently H or acetyl; and X is —$CHX_2PO_3H_2$ or —$CHX_2P(O)R_6OH$.

11. A herbicidal composition comprising a herbicidally effective amount of a compound of claim 1 in association with an agriculturally acceptable diluent.

12. A method of controlling undesirable plant growth comprising applying to the undesirable plant growth or area wherein said undesirable plants are growing a herbicidally effective amount of a compound of claim 1.

13. A compound of the formula

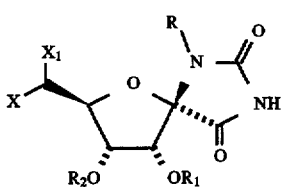

wherein

R, $R_1$ and $R_2$ are independently H and lower alkylcarbonyl;

$X_1$ is H;

X is —$SC(O)R_3$, —$OSO_2R_3$, —$OPO_3(R_7)_2$, $N_3$, $R_4R_5NO$, —$ONO_2$, —$P(O)R_6OH$, —$CHX_2PO_3H_2$, or $CHX_2P(O)R_6OH$;

$R_3$ is lower alkyl or lower haloalkyl;

$R_4$ and $R_5$ are independently H and lower alkylcarbonyl or $R_4$ and $R_5$ taken together form phthaloyl;

$R_6$ is H, OH or lower alkyl;

$R_7$ is H, alkali or alkaline earth cation, ammonium cation or substituted ammonium cation; and $X_2$ is H or halogen.

14. A compound according to claim 13 wherein X is —$SC(O)R_3$, —$OSO_2R_3$, —$OPO_3H_2$, $R_4R_5NO$ or —$P(O)R_6OH$.

15. A compound of the formula

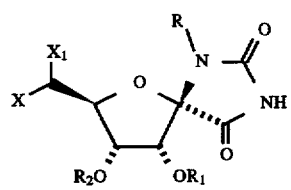

wherein

R is acetyl; $R_1$ and $R_2$ are independently acetyl or H; $X_1$ is hydrogen or fluoro; X is halogen, —$SC(O)R_3$, —$OPO_3H_2$, —$OPO_3Na_2$, —$OSO_2R_3$, —$ONO_2$, $N_3$, —$P(O)R_6OH$ and $R_4R_5NO$; $R_3$ is $CH_3$ or $CF_3$; $R_4$ and $R_5$ taken together form phthaloyl and $R_6$ is H, OH or ($C_1$–$C_4$) alkyl.

16. A compound according to claim 14 wherein R, $R_1$, and $R_2$, are acetyl; $X_1$ is H and X is —$OPO_3H_2$, —$OSO_2R_3$, or —$SC(O)R_3$.

17. A herbicidal composition comprising a herbicidally effective mount of a compound of claim 15 in association with an agriculturally acceptable diluent.

18. The composition of claim 11 wherein the composition is applied post-emergence.

19. The composition of claim 17 wherein the composition is applied post-emergence.

20. A compound according to claim 14 wherein X is $CHX_2PO_3H_2$ or $CHX_2P(O)R_6OH$.

21. A compound according to claim 15 wherein $X_1$ is H and X is halogen.

* * * * *